(12) United States Patent
Yamano et al.

(10) Patent No.: US 10,416,123 B2
(45) Date of Patent: Sep. 17, 2019

(54) FLAW DETECTION SENSITIVITY ADJUSTMENT METHOD AND ABNORMALITY DIAGNOSIS METHOD FOR ULTRASONIC PROBE

(71) Applicant: NIPPON STEEL & SUMITOMO METAL CORPORATION, Tokyo (JP)

(72) Inventors: Masaki Yamano, Tokyo (JP); Yoshiyuki Nakao, Tokyo (JP); Shigetoshi Hyodo, Tokyo (JP); Masaki Tanaka, Tokyo (JP); Tsukasa Suda, Tokyo (JP)

(73) Assignee: NIPPON STEEL CORPORATION, Tokyo (JP)

( * ) Notice: Subject to any disclaimer, the term of this patent is extended or adjusted under 35 U.S.C. 154(b) by 38 days.

(21) Appl. No.: 14/401,896

(22) PCT Filed: May 17, 2013

(86) PCT No.: PCT/JP2013/063737
§ 371 (c)(1),
(2) Date: Nov. 18, 2014

(87) PCT Pub. No.: WO2013/176039
PCT Pub. Date: Nov. 28, 2013

(65) Prior Publication Data
US 2015/0135799 A1    May 21, 2015

(30) Foreign Application Priority Data

May 23, 2012  (JP) ................................ 2012-117876

(51) Int. Cl.
*G01N 29/30* (2006.01)
*G01N 29/04* (2006.01)
(Continued)

(52) U.S. Cl.
CPC .............. *G01N 29/30* (2013.01); *G01N 29/04* (2013.01); *G01N 29/11* (2013.01); *G01N 29/275* (2013.01);
(Continued)

(58) Field of Classification Search
CPC ........ G01N 29/34; G01N 29/30; G01N 29/04; G01N 29/11; G01N 29/275;
(Continued)

(56) References Cited

U.S. PATENT DOCUMENTS 4,462,082 A * 7/1984 Thiele ................ G01N 29/4463
367/13
7,389,692 B2 * 6/2008 Cuffe ..................... G01N 29/36
600/437

(Continued)

FOREIGN PATENT DOCUMENTS

JP    53-091793    8/1978
JP    60-260850    12/1985
(Continued)

OTHER PUBLICATIONS

English translation of JP 2006-047328, included on the IDS filed Nov. 19, 2014.*
(Continued)

*Primary Examiner* — Justin Seo
*Assistant Examiner* — John M Royston
(74) *Attorney, Agent, or Firm* — Clark & Brody (57) ABSTRACT

A method of adjusting flaw detection sensitivity on an array ultrasonic probe comprises disposing a plate material P1 oppositely to the ultrasonic probe such that an upper surface of the plate material is disposed to be approximately parallel to an array direction of the transducers 11, or disposing a tubular material P2 oppositely to the ultrasonic probe such that an axial direction of the tubular material is disposed to
(Continued)

be approximately parallel to the array direction of the transducers. Ultrasonic waves are transmitted from each transducer toward the upper surface of the plate material or an outer surface of the tubular material, and echoes are received from the bottom surface of the plate material or an inner surface of the tubular material on each transducer. Flaw detection sensitivity of each transducer is adjusted to substantially equalize intensity of an echo received on each transducer.

2 Claims, 8 Drawing Sheets

(51) Int. Cl.
    *G01N 29/275* (2006.01)
    *G01N 29/11* (2006.01)
(52) U.S. Cl.
    CPC . *G01N 2291/044* (2013.01); *G01N 2291/106* (2013.01); *G01N 2291/2632* (2013.01); *G01N 2291/2634* (2013.01)
(58) Field of Classification Search
    CPC ....... G01N 2291/044; G01N 2291/106; G01N 2291/2632; G01N 2291/2634
    See application file for complete search history.

(56) References Cited

U.S. PATENT DOCUMENTS

| | | | | |
|---|---|---|---|---|
| 7,966,860 B2* | 6/2011 | Dijkstra | ............... | G01N 29/225 73/1.82 |
| 2009/0217763 A1* | 9/2009 | Yamano | ............... | G01N 29/043 73/622 |
| 2011/0283798 A1* | 11/2011 | Yamano | ............... | G01N 29/043 73/632 |

FOREIGN PATENT DOCUMENTS

| | | |
|---|---|---|
| JP | 61-070459 | 4/1986 |
| JP | 5-188138 | 7/1993 |
| JP | 6-125901 | 5/1994 |
| JP | 10-227769 | 8/1998 |
| JP | 10-227772 | 8/1998 |
| JP | 11-160293 | 6/1999 |
| JP | 2006-047328 | 2/2006 |

OTHER PUBLICATIONS

JIS Z 2350: 2002, "Method for measurement . . . of ultrasonic probes", Japanese Industrial Standard.

\* cited by examiner

FLAW DETECTION SENSITIVITY ADJUSTMENT METHOD AND ABNORMALITY DIAGNOSIS METHOD FOR ULTRASONIC PROBE

TECHNICAL FIELD

The present invention relates to a method of appropriately adjusting flaw detection sensitivity of an ultrasonic probe including multiple transducers aligned in a certain direction and a method of appropriately diagnosing abnormality of the same.

BACKGROUND ART

When performing flaw detection using an ultrasonic probe including multiple transducers aligned in a one direction, each of which is fixed to one another (referred to as an array ultrasonic probe, hereinafter), in transducers (n>m≥1) are selected among n (n≥2) transducers included in the array ultrasonic probe, and the selected transducers transmit ultrasonic waves toward a test material and the selected transducers receive echoes returned from this test material. Echoes received on the respective transducers of the selected transducers are synthesized, and the synthesized waveform is used for the flaw detection on the test material. This procedure is repetitively executed by changing over different units of the selected transducers. Hence, it is important to appropriately evaluate the relative sensitivity of each transducer and appropriately adjust the flaw detection sensitivity of each transducer, which is amplification degree of the echo signal. Specifically, it is important to adjust the flaw detection sensitivity of each transducer such that equal echo intensity is obtained among the respective transducers if each transducer receives an echo from the same artificial flaw.

Such a method for evaluating an array ultrasonic probe is not yet specified by the JIS standard or others at the present time. Hence, it is common to evaluate the performance in compliance with the JIS standard regarding the performance evaluation method, of an immersion normal probe with a single transducer as described in non-Patent Literature 1. Specifically, this method includes a method for evaluation of frequency response using a top surface echo from a flat plate specimen set forth in Section 7.1, a method for evaluation of relative sensitivity using a top surface echo from a flat plate specimen set forth in Section 7.3, and a method for evaluation of beam profile and distance amplitude characteristics using a steel ball with a diameter of ϕ 4 mm or a steel wire with a diameter of ϕ 2.5 mm set forth in Section 8.5.1 of non-Patent Literature 1, respectively.

As mentioned above, flaw detection using an array ultrasonic probe is performed by changing over different units of the selected transducers. Specifically, in performing flaw detection using an array ultrasonic probe, the flaw detection is carried out on each of different units of the selected transducers. As an abnormality diagnosis method for an array ultrasonic probe, such a method has been practiced that carries out flaw detection on a predetermined artificial flaw on every unit of selected transducers, and if the intensity of a resulted synthesized waveform is more than a predetermined allowed value, no abnormality such as malfunction occurs on the transducers of the array ultrasonic probe.

CITATION LIST

Patent Literature

[Non-Patent Literature 1] JIS Z2350 "Method for measurement of performance characteristics of ultrasonic probes"

SUMMARY OF INVENTION

Technical Problem

Unfortunately, the present inventors have recognized that it is difficult to appropriately evaluate performance of an array ultrasonic probe by using the above mentioned performance evaluation method in compliance with the MS standard. Specifically, in the method using a top surface echo from a flat plate specimen, it is difficult to appropriately evaluate relative sensitivity and appropriately adjust flaw detection sensitivity of each transducer, as described later. In the method using a steel ball with a diameter of ϕ 4 mm or a steel wire with a diameter of ϕ 2.5 mm, it is feasible to appropriately evaluate relative sensitivity and appropriately adjust flaw detection sensitivity of each transducer, as described later; but the procedures required for the evaluation and the adjustment become too complicated. Consequently, it is substantially difficult to work on the flaw detection, particularly in a state where an array ultrasonic probe is installed in an inspection line. The present inventors have also recognized that an abnormality of an array ultrasonic probe cannot be sufficiently detected simply by monitoring deterioration of intensity of a synthesized waveform, as described in the above abnormality diagnosis method.

The aforementioned difficulties may occur not only on an array ultrasonic probe, but also on another ultrasonic probe including multiple transducers aligned in one direction such as an ultrasonic probe having multiple probes with a single transducer in alignment with one another.

An object of the present invention, which has been made in order to solve the difficulties according to the conventional art described above, is to provide a method of appropriately adjusting flaw detection sensitivity of an ultrasonic probe including multiple transducers aligned in a certain direction and a method of appropriately diagnosing abnormality of the same, particularly to provide these methods applicable even in a state where the ultrasonic probe is installed in an inspection line.

Solution to Problem

The present inventors earnestly studied on a method of appropriately adjusting flaw detection sensitivity of ultrasonic probe including multiple transducers aligned in a certain direction, and obtained the following finding and has completed the present invention: the distribution characteristics of echo intensity among the respective transducers in the case of receiving an echo from a bottom surface of a plate material or an inner surface of a tubular material on each transducer is correspondent to the distribution characteristics of echo intensity among the respective transducers in the case of receiving an echo from the same artificial flaw on each transducer.

In order to achieve the object, the present invention provides a method of adjusting flaw detection sensitivity on an ultrasonic probe including multiple transducers aligned in a certain direction, the method comprising: a step of disposing a plate material oppositely to the ultrasonic probe such that an upper surface of the plate material having the upper surface and a bottom surface that are approximately parallel to each other is disposed to be approximately parallel to an array direction of the transducers, or disposing a tubular material oppositely to the ultrasonic probe such that an axial direction of the tubular material is disposed to be approximately parallel to the array direction of the transducers; a step of transmitting ultrasonic waves from each transducer toward the upper surface of the plate material or an outer surface of the tubular material, and receiving echoes from the bottom surface of the plate material or an inner surface of the tubular material on each transducer; and a step of adjusting flaw detection sensitivity of each transducer so as to substantially equalize intensity of an echo received on each transducer.

As mentioned above, the distribution characteristics of echo intensity among the respective transducers in the case of receiving an echo from a bottom surface of a plate material or an inner surface of a tubular material on each transducer is correspondent to the distribution characteristics of echo intensity among the respective transducers in the case of receiving an echo from the same artificial flaw on each transducer. According to the present invention, the respective transducers transmits ultrasonic waves toward an upper surface of a plate material or an outer surface of a tubular material, and adjusts the flaw detection sensitivity of each transducer such that echo intensities received on the respective transducers is substantially equal to one another; thus it may be expected that echo intensities of echoes from the same artificial flaw received on the respective transducers after adjusted also is substantially equal to one another. In other words, the present invention can appropriately adjust the flaw detection sensitivity of each transducer included in the ultrasonic probe.

The respective sizes of the plate material and the tubular material in the array direction of the transducers are preferably equal to or more than the size of transducers of the ultrasonic probe in the array direction of the transducers.

In this preferable configuration, it is unnecessary to relatively scan the plate material or the tubular material by the ultrasonic probe in the array direction of the transducers, and every transducer can receive an echo from the bottom surface of the plate material or the inner surface of the tubular material, which facilitates the adjustment of the flaw detection sensitivity, and it is particularly suitable to the adjustment of an ultrasonic probe installed in an inspection line.

The present inventors earnestly studied on a method of appropriately diagnosing abnormality of an ultrasonic probe including multiple transducers aligned in a certain direction, and obtained the following finding: if malfunction occurs on any transducer of the selected transducers, in which a transmitting and receiving function cannot work, decrease in the effective beam width of the selected transducers relative to the measurement target occurs prior to decrease in the intensity of the synthesized waveform of echoes from the measurement target received on the respective transducers of the selected transducer. In an intensity profile of a synthesized waveform of echoes obtained from the measurement target when the selected transducers relatively scan in the array direction of the transducers, the effective beam width denotes a length of a range where the intensity of the synthesized waveform is at a predetermined intensity or more (for example, −6 dB at the maximum intensity of 0 dB).

Figure 1A:
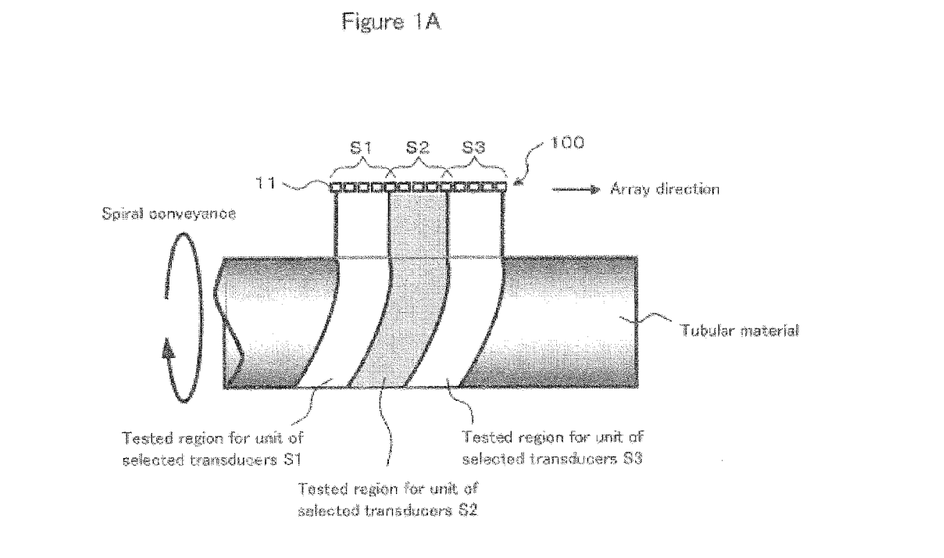
FIGS. 1A and 1B illustrate a state of performing flaw detection by allowing an array ultrasonic probe to relatively scan in a direction vertical to an array direction of transducers.
Figure 1B:
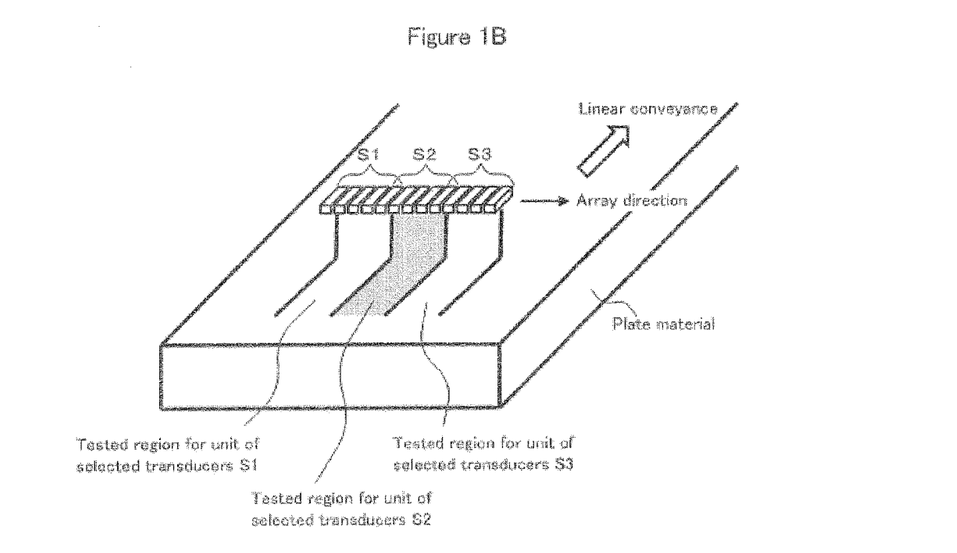

As illustrated in FIG. 1, in the case of allowing the ultrasonic probe 100 to relatively scan in the vertical direction to the array direction of the transducers 11 (FIG. 1A illustrates the flaw detection on the tubular material, and FIG. 1B illustrates the flaw detection on the plate material), if the effective beam width decreases excessively, the effective beam width of one unit of the selected transducers S1 does not overlap that of its adjacent unit of the selected transducers S2, so that a gap therebetween acts as an untested region where a flaw may be undetected. The same occurs between the unit of the selected transducers S2 and its adjacent unit of the selected transducers S3.

The present inventors obtained such a finding that the above described difficulty cannot be sufficiently foreseen only by monitoring the decrease in the intensity of the echo synthesized waveform because such decrease in the effective beam width occurs prior to the decrease in the intensity of the echo synthesized waveform as described above. Accordingly, the present inventors considered that, in order to appropriately diagnose abnormality of transducers included in every unit of the selected transducers, it is important to determine whether or not the effective beam width thereof is equal to a predetermined threshold value or less. The present inventors have completed the present invention based on the above described findings.

In order to achieve the object, the present invention provides a method of diagnosing abnormality for an ultrasonic probe including n (n≥2) transducers aligned in a certain direction, the method comprising the following first-fourth steps.

(1) A First Step

Selecting m (n>m≥1) transducers among the n transducers, transmitting ultrasonic waves from the selected transducers toward a measurement target, and receiving echoes from the measurement target on the selected transducers (2) A Second Step Relatively scanning the measurement target by the selected transducers in an array direction of the transducers, and calculating an effective beam width of the selected transducers relative to the measurement target (3) A Third Step Repetitively executing the first step and the second step alternatively by changing over multiple units of the selected transducers one by one (4) A Fourth Step Determining, if any of effective beam widths of the multiple units of the selected transducers obtained in the third step is equal to a predetermined threshold value or less, that abnormality occurs on a unit of the selected transducers having the effective beam width equal to the predetermined threshold value or less According to the above described invention, it is possible to approximately diagnose abnormality of the ultrasonic probe.

Advantageous Effects of Invention

According to the present invention, it is possible to appropriately adjust the flaw detection sensitivity of an ultrasonic probe including multiple transducers aligned in a certain direction and to appropriately diagnose abnormality of the ultrasonic probe. In particular, it is possible to adjust the flaw detection sensitivity and to diagnose abnormality of the ultrasonic probe even in a state in which the ultrasonic probe is installed in an inspection line.

DESCRIPTION OF EMBODIMENT

Hereinafter, description will be provided on one embodiment of the present invention with reference to the accompanying drawings.

<Flaw Detection Sensitivity Adjustment Method for Ultrasonic Probe>

A flaw detection sensitivity adjustment method according to the present embodiment is a method of adjusting flaw detection sensitivity (amplification degree of an echo signal) of an array ultrasonic probe.

Figure 2A:
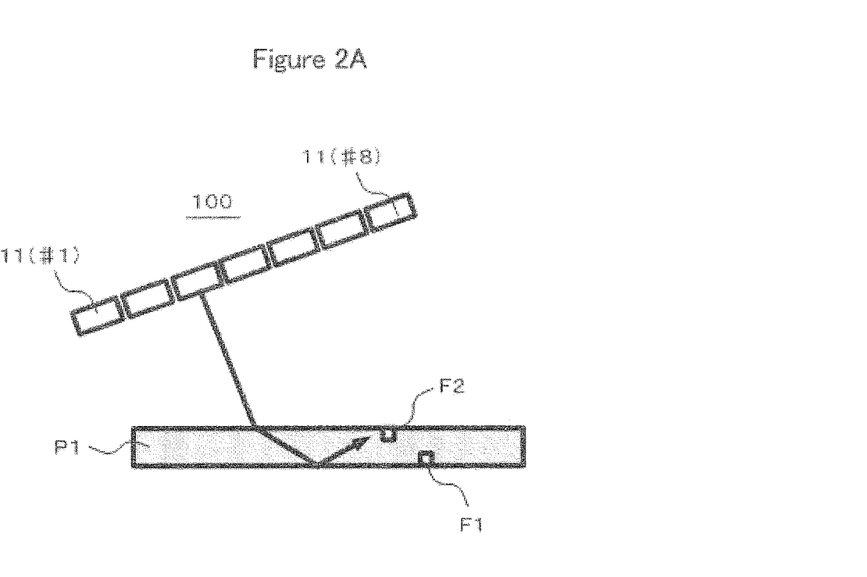
FIGS. 2A and 2B illustrate one example of correction amount of flaw detection sensitivity required in the angle beam testing using the array ultrasonic probe.
Figure 2B:
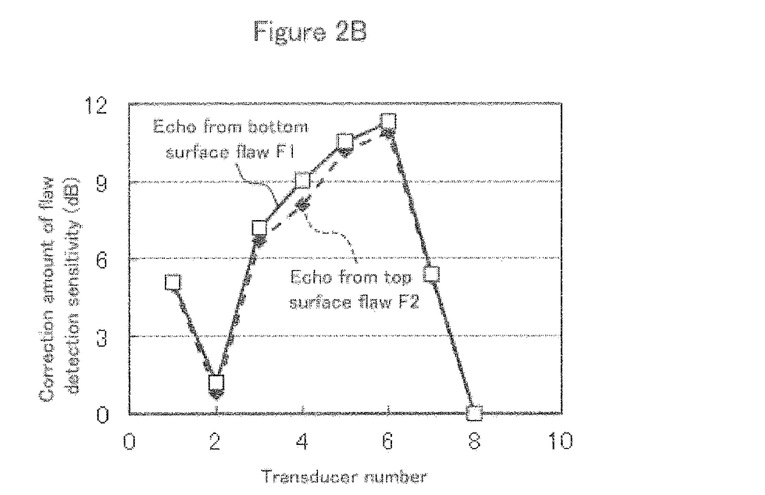

FIGS. 2A and 2B illustrate one example of correction amount of flaw detection sensitivity required in the angle beam testing using the array ultrasonic probe. FIG. 2A is an explanatory view of explaining the outline of the angle beam testing, and FIG. 2B shows the amount of correction of flaw detection sensitivity required for each transducer.

Specifically, as illustrated in FIG. 2A, notches F1 and F2 are formed in an upper surface and a bottom surface of a plate material P1 having the upper surface and the bottom surface which are approximately parallel to each other. The array ultrasonic probe 100 is disposed oppositely to the upper surface of this plate material P1 with the array direction of transducers 11 (eight transducers #1 to #8) set to be inclined. Then, every transducer #1 to #8 transmits ultrasonic wave relative to the upper surface of the plate material P1 and every transducer #1 to #8 receives echoes from the notches F1 and F2. At this time, the plate material P1 is scanned in the right and left direction so that echoes from the notches F1 and F2 are received on every transducer #1 to #8.

The correction amount of flaw detection sensitivity represented by the ordinate of FIG. 2B denotes the correction amount of flaw detection sensitivity required to substantially equalize the intensity of an echo received on each transducer #1 to #8. For example, if the correction amount of flaw detection sensitivity is 6 dB, this means that the flaw detection sensitivity (amplification degree of an echo signal) should be about twice as strong as the flaw detection sensitivity before corrected. As apparent from FIG. 2B, the distribution characteristics of the echo intensity among the respective transducers #1 to #8 before the flaw detection sensitivity is corrected is equal between the notch F1 on the bottom surface and the notch F2 on the upper surface.

The present inventors made a comparison test between the above described evaluation method using the artificial flaws and other evaluation methods. The present inventors studied on a method using a top surface echo from a plate material and a method using a top surface (outer surface) echo from a tubular material (outer diameter of 114 mm, wall thickness of 7.5 mm), both in compliance with the JIS standard.

Figure 3A:
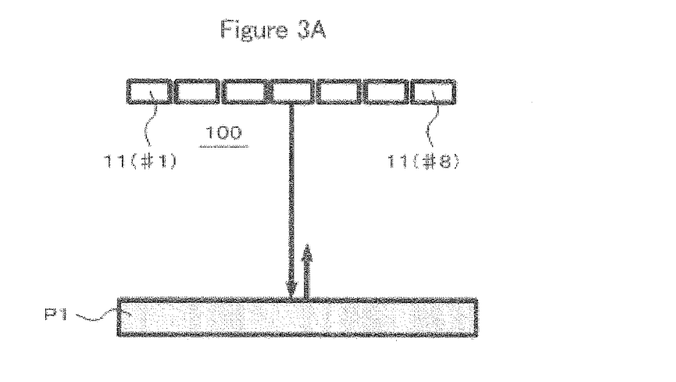
FIGS. 3A to 3C illustrate one example of the correction amount of flaw detection sensitivity that was required when receiving the top surface echoes from the plate material and the tubular material on the array ultrasonic probe.
Figure 3B:
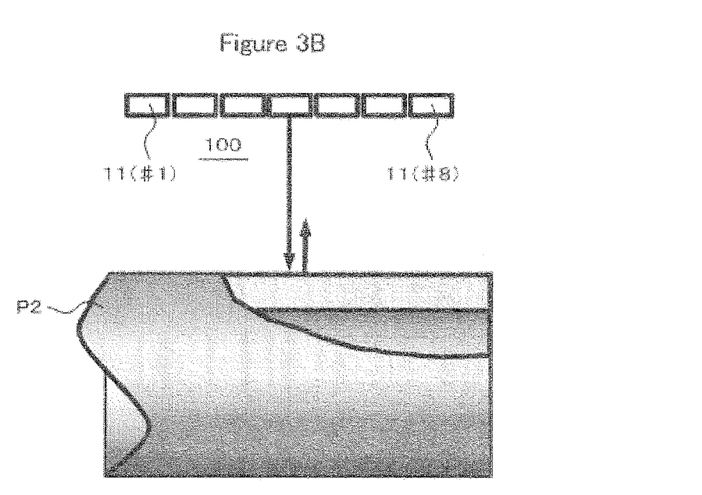
Figure 3C:
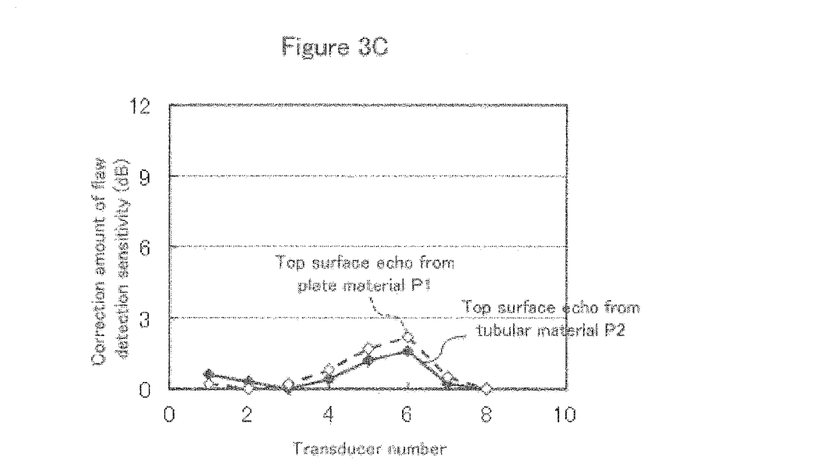

FIGS. 3A to 3C illustrate one example of the correction amount of flaw detection sensitivity that was required when receiving the top surface echoes from the plate material and the tubular material on the array ultrasonic probe. FIG. 3A is an explanatory view of explaining the outline of the evaluation test using a top surface echo from the plate material, FIG. 3B is an explanatory view of explaining the outline of the evaluation test using a top surface echo from the tubular material, and FIG. 3C shows the correction amount of flaw detection sensitivity required for each transducer.

Specifically, in the case of using a top surface echo from the plate material, as illustrated in FIG. 3A, the array ultrasonic probe 100 was disposed such that the array direction of the transducers 11 (eight transducers #1 to #8) was opposed approximately parallel to the surface of the plate material P1 having the upper surface and the bottom surface that are approximately parallel to each other. Then, every transducer #1 to #8 transmits ultrasonic waves relative to the upper surface of the plate material P1, and every transducer #1 to #8 receives echoes from the upper surface of the plate material P1.

As illustrated in FIG. 3B, in the case of using a top surface echo from the tubular material, the array ultrasonic probe 100 was disposed such that the array direction of the transducers 11 (eight transducers #1 to #8) was opposed approximately parallel to the axial direction of the tubular material P2. Then, every transducer #1 to #8 transmits ultrasonic waves relative to the outer surface of the tubular material P2 and every transducer #1 to #8 receives echoes from the outer surface of the tubular material P2.

The correction amount of law detection sensitivity represented by the ordinate of FIG. 3C has the same meaning as that illustrated in FIG. 2B, and denotes the correction amount of flaw detection sensitivity required to substantially equalize the intensity of an echo received on every transducer #1 to #8. As apparent from FIG. 3C, the distribution characteristics of the echo intensity among the respective transducers #1 to #8 before the flaw detection sensitivity was corrected was equal between the plate material P1 and the tubular material P2. It should be appreciated from the comparison between FIG. 3C and FIG. 2B that the distribution characteristics of the echo intensity in FIG. 3C is not correspondent to the distribution characteristics of the echo intensity in FIG. 2B. This means that, even if the flaw detection sensitivity of each transducer #1 to #8 is adjusted in accordance with the result in FIG. 3C, the echo intensity of the echo from the artificial flaw received, on each transducer #1 to #8 cannot be substantially equalized among the transducers #1 to #8; that is, the flaw detection sensitivity cannot be adjusted appropriately.

The present inventors also studied on the above mentioned method using an echo from a steel ball with a diameter of ϕ 4 mm set forth in the JIS standard.

Figure 4A:
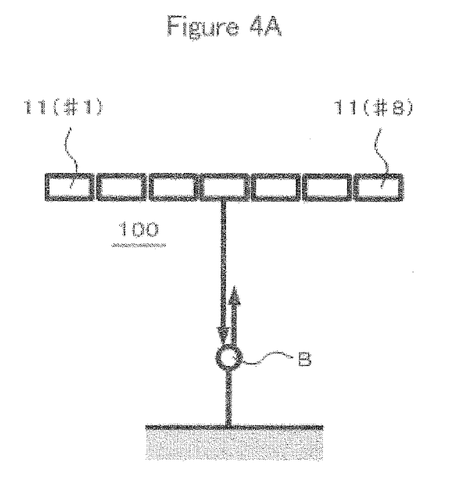
FIGS. 4A and 4B illustrate one example of the correction amount of flaw detection sensitivity required when an echo from the steel ball with a diameter of ϕ4 mm is received on the array ultrasonic probe.
Figure 4B:
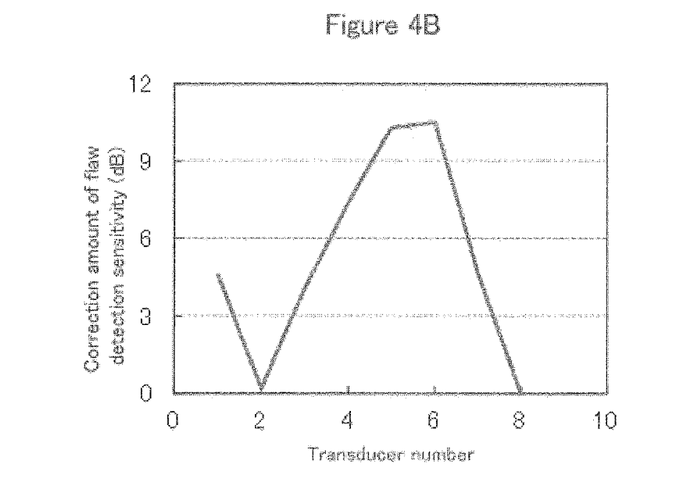

FIGS. 4A and 4B illustrate one example of the correction amount of flaw detection sensitivity required when an echo from the steel ball with a diameter of ϕ 4 mm is received on the array ultrasonic probe. FIG. 4A is an explanatory view of explaining the outline of the evaluation test using an echo from the steel ball with a diameter of ϕ 4 mm, and FIG. 4B shows the correction amount of flaw detection sensitivity required for each transducer.

Specifically, as illustrated in FIG. 4A, the array ultrasonic probe 100 was disposed oppositely to the steel ball B with a diameter of ϕ 4 mm, and ultrasonic waves were transmitted from the respective transducers #1 to #8 toward the steel ball B with a diameter of ϕ 4 mm, and echoes from the steel ball B with a diameter of ϕ 4 mm were received on the respective transducers #1 to #8. At this time, either of the array ultrasonic probe 100 and the steel ball B with a diameter of ϕ 4 mm was moved for the scanning in the right and left direction in FIG. 4A at appropriate timing such that the steel ball B with a diameter of ϕ 4 mm was located immediately beneath the transducers 11 that transmit and receive ultrasonic waves.

The correction amount of flaw detection sensitivity of the ordinate in FIG. 4B has the same meaning as that illustrated in FIG. 2B, and denotes the correction amount of flaw detection sensitivity required to substantially equalize the intensity of an echo received on every transducer #1 to #8. It should be appreciated from the comparison between FIG. 4B and FIG. 2B that the distribution characteristics of the echo intensity in FIG. 4B is correspondent to the distribution characteristics of the echo intensity in FIG. 2B. This means that, if the flaw detection sensitivity of each transducer #1 to #8 is adjusted in accordance with the result in FIG. 4B, the echo intensity of an echo from the artificial flaw received on each transducer #1 to #8 can be substantially equalized. Unfortunately, either of the array ultrasonic probe 100 and the steel ball B with a diameter of ϕ 4 mm should be moved for the scanning at appropriate timing so that the steel ball B with a diameter of ϕ 4 mm is located immediately beneath the transducers 11 transmitting and receiving ultrasonic waves, which makes the evaluation procedure complicated, and particularly, it is substantially difficult to work on the flaw detection with the array ultrasonic probe installed in an inspection line.

The present inventors farther earnestly studied on the method using a bottom surface echo from the plate material and the method using a bottom surface (inner surface) echo from the tubular material (outer diameter of ϕ 114 mm, wall thickness of 7.5 mm).

Figure 5A:
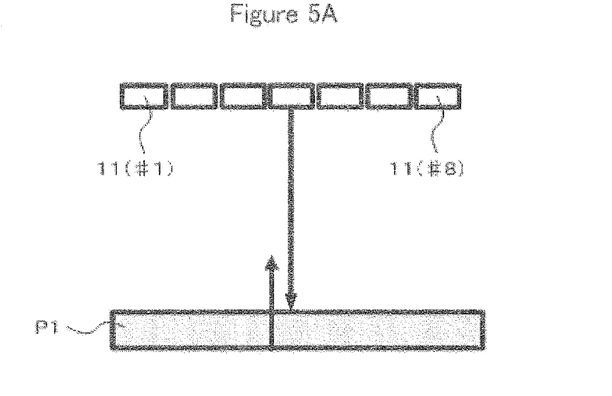
FIGS. 5A to 5C illustrate one example of the correction amount of flaw detection sensitivity required when receiving bottom surface echoes from the plate material and the tubular material by means of the array ultrasonic probe.
Figure 5B:
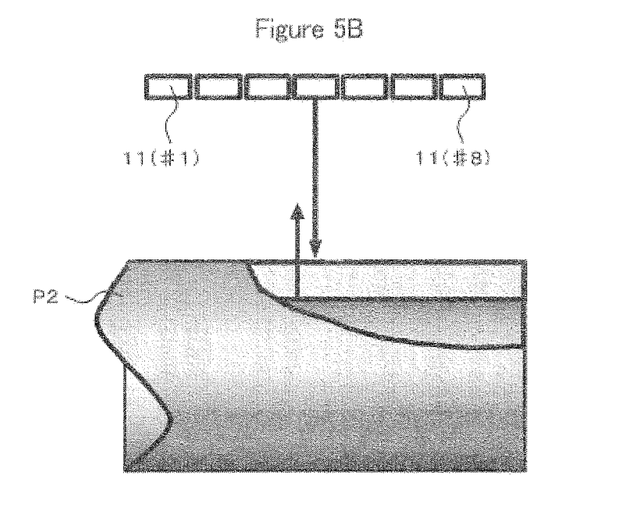
Figure 5C:
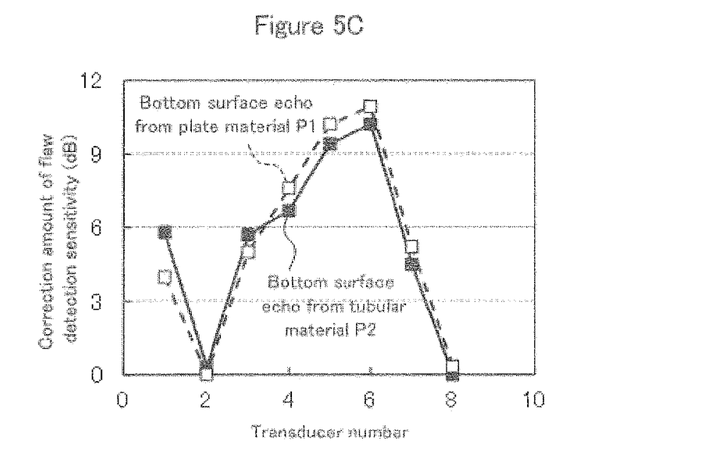

FIGS. 5A to 5C illustrate one example of the correction amount of flaw detection sensitivity required when receiving bottom surface echoes from the plate material and the tubular material by means of the array ultrasonic probe. FIG. 5A is an explanatory view of explaining the outline of the evaluation test using a bottom surface echo from the plate material, FIG. 5B is an explanatory view of explaining the outline of the evaluation test using a bottom surface echo from the tubular material, and FIG. 5C shows the correction amount of flaw detection sensitivity required for each transducer.

Specifically, in the case of using a bottom surface echo from the plate material, as illustrated in FIG. 5A, the array ultrasonic probe 100 was disposed such that the array direction of the transducers 11 (eight transducers #1 to #8) was opposed approximately parallel to the surface of the plate material P1 having the upper surface and the bottom surface that are approximately parallel to each other. Then, every transducer #1 to #8 transmitted ultrasonic waves relative to the upper surface of the plate material P1, and every transducer #1 to #8 received echoes from the bottom surface of the plate material P1.

As illustrated in FIG. 5B, in the case of using the bottom surface echo from the tubular material, the array ultrasonic probe 100 was disposed such that the array direction of the transducers 11 (eight transducers #1 to #8) was opposed approximately parallel to the axial direction of the tubular material P2. Then, every transducer #1 to #8 transmitted ultrasonic waves relative to the outer surface of the tubular material P2, and every transducer #1 to #8 received echoes from the inner surface of the tubular material P2.

The correction amount of flaw detection sensitivity of the ordinate in FIG. 5C has the same meaning as that illustrated in FIG. 2B, and denotes the correction amount of flaw detection sensitivity required to substantially equalize the echo intensity of an echo received on every transducer #1 to #8. As apparent from FIG. 5C, the distribution characteristics of the echo intensity among the respective transducers #1 to #8 before the flaw detection sensitivity was corrected was equal between the plate material P1 and the tubular material P2. It should be appreciated from the comparison between FIG. 5C and FIG. 2B that the distribution characteristics of the echo intensity in FIG. 5C is correspondent to the distribution characteristics of the echo intensity in FIG. 2B. This means that, the echo intensity of an echo from the artificial flaw received on each transducer #1 to #8 can be substantially equalized by adjusting the flaw detection sensitivity of each transducer #1 to #8 in accordance with the result in FIG. 5C, which means that the flaw detection sensitivity can be adjusted appropriately.

Based on the above described studies, the flaw detection sensitivity adjustment method according to the present embodiment includes: a step of disposing the plate material P1 oppositely to the array ultrasonic probe 100 such that the upper surface of the plate material P1 having the upper surface and the bottom surface that are approximately parallel to each other is disposed to be approximately parallel to the array direction of the transducers 11, or disposing the tubular material P2 oppositely to the array ultrasonic probe 100 such that the axial direction of the tubular material P2 is disposed to be approximately parallel to the array direction of the transducers 11; a step of transmitting ultrasonic waves from each transducer 11 toward the upper surface of the plate material P1 or the outer surface of the tubular material P2 and receiving echoes from the bottom surface of the plate material P1 or the inner surface of the tubular material P2 on each transducer 11; and a step of adjusting the flaw detection sensitivity (amplification degree of echo signal) of each transducer 11 so as to substantially equalize the intensity of an echo received on each transducer 11.

In the method of using a top surface echo from the plate material P1 and in the method of using a top surface (outer surface) echo from the tubular material P2 (see FIG. 3), both in compliance with the JIS standard as described above, the distribution characteristics of the echo intensity before corrected is not equivalent to those of the echo intensity before corrected in the angle beam testing (see FIG. 2); and in the method of using a bottom surface echo from the plate material P1 or in the method of using a bottom surface (inner surface) echo from the tubular material P2 (see FIG. 5), the distribution characteristics of the echo intensity before corrected is equivalent to those of the echo intensity before corrected in the angle beam testing (see FIG. 2). The reasons for these findings may be concluded as follows.

In the array ultrasonic probe 100 whose multiple transducers 11 are fixed to one another (the transducers 11 are never displaced relative to one another), it may be considered that every transducer 11 is slightly inclined. In particular, it becomes almost impossible to align the inclination of every transducer 11 in a constant direction if there are more and more transducers 11 in the probe. Hence, it may be considered that the orientation of ultrasonic waves transmitted from every transducer 11 varies slightly. When performing the angle beam testing, an ultrasonic wave is refracted at the incident point into the test material and propagates through inside the test material. It may be considered that the refraction angle varies depending on the incident angle, and if the orientation of the ultrasonic wave transmitted from each transducer 11 varies among the transducers 11, variation in the orientation of an ultrasonic wave refracted at the incident point and propagating through inside the test material may become more significant among the respective transducers 11. This may result in more significant variation in the distribution characteristics of the echo intensity before corrected.

Similarly, in the method of using a bottom surface echo of, the plate material P1 or the tubular material P2, while an ultrasonic wave transmitted from every transducer 11 is propagating through insides of the plate material P1 or the tubular material P2, variation in the orientation of the ultrasonic wave becomes magnified, resulting in greater variation in the distribution characteristics of the echo intensity before corrected among the transducers 11.

To the contrary, in the method of using a top surface echo of the plate material P1 or the tubular material P2, an echo of an ultrasonic wave transmitted from every transducer 11 is received before propagating through inside the plate material P1 and the tubular material P2 (non-refractive echoes) so that variation in the distribution characteristics of the echo intensity before corrected becomes smaller in comparison with the case of using an bottom surface echo thereof.

<Abnormality Diagnosis Method for Ultrasonic Probe>

The abnormality diagnosis method according to the present embodiment diagnoses abnormality of the array ultrasonic probe including n (n≥2) transducers.

In the flaw detection using the array ultrasonic probe of the present embodiment, in (n>m≥1) transducers are selected among the n transducers, and ultrasonic waves are transmitted from these selected transducers toward a measurement target and echoes are received from the measurement target on the selected transducers. Echoes received on the respective transducers of the selected transducers are synthesized and this synthesized wave is used for the flaw detection on the measurement target. This procedure is repetitively executed on every unit of the selected transducers by changing over the different units of the selected transducers one by one.

The abnormality diagnosis method according to the present embodiment diagnoses abnormality based on the determination of whether or not the effective beam width of the selected transducers relative to the measurement; target is equal to a predetermined threshold value or less.

Figure 6:
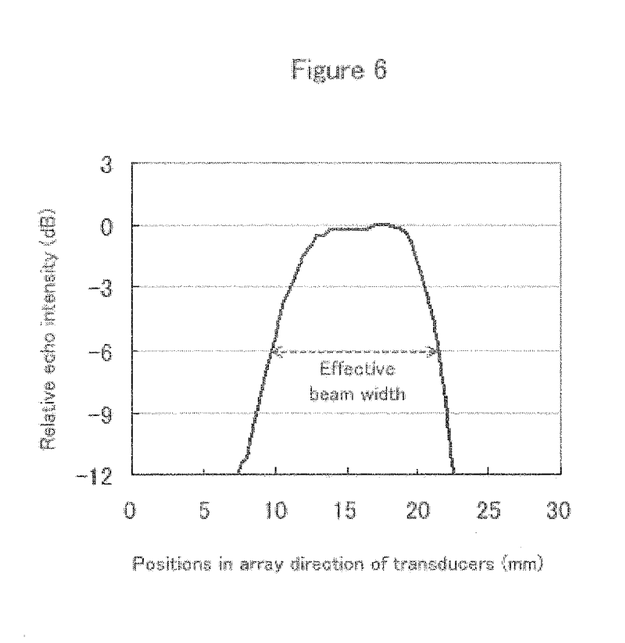
FIG. 6 is an explanatory view of explaining what the effective beam width means.

FIG. 6 is an explanatory view of explaining what the effective beam width means.

The graph represented by a solid line in FIG. 6 shows one example of a profile of the echo intensity (intensity of a synthesized wave of echoes) obtained from the measurement target relatively scanned by the selected transducers in the array direction of the transducers (for example, the measurement target is scanned by the selected transducers by allowing the array ultrasonic probe to mechanically scan (move relative to) the measurement target). In this profile, the effective beam width denotes a length in a range where the echo intensity is a predetermined intensity or more (for example, −6 dB at the maximum intensity of 0 dB).

Figure 7:
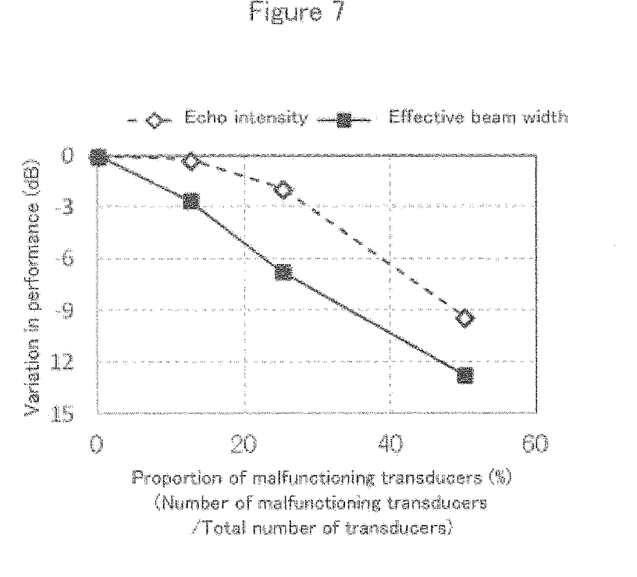
FIG. 7 shows one example of the relations between the proportion of malfunctioning transducers among the selected transducers and the intensity of the echo received on the selected transducers and the relation between the proportion of malfunctioning transducers among the selected transducers and the effective beam width of the selected transducers.

FIG. 7 shows one example of the relations between the proportion of malfunctioning transducers among the selected transducers and the intensity of the echo (intensity of a synthesized wave of echoes) received on the selected transducers and the relation between the proportion of malfunctioning transducers among the selected transducers and the effective beam width of the selected transducers.

Specifically, malfunctioning transducers were simulated by using 16 transducers as the selected transducers, and stopping supply of transmission voltage (voltage of a pulse signal for transmitting an ultrasonic waves from each transducer) to the simulated malfunctioning transducers, or stopping input to a waveform synthesis circuit (circuit for synthesizing echo signals received on the respective transducers) for echo signals received on the simulated malfunctioning transducers.

A steel ball with a diameter of $\phi$ 4 mm was used as the measurement target, and the selected transducers were disposed oppositely to the steel ball with a diameter of $\phi$ 4 mm, as similar to the manner in FIG. 4A. Toward the steel ball with a diameter of $\phi$ 4 mm, ultrasonic waves were transmitted from and received on the transducers other than the simulated malfunctioning transducers among the selected transducers at the approximately same timing, so as to measure intensity of the synthesized waveform of the echoes. In addition, the selected transducers were allowed to relatively scan in the array direction of the transducers, and a profile of the echo intensity (intensity of synthesized waveform of echoes) as similar to that in FIG. 6 was calculated.

The above mentioned procedure was repetitively executed using various numbers of malfunctioning transducers.

The echo intensity shown in FIG. 7 denotes the maximum intensity in the profile of the intensity of synthesized waveform of echoes calculated through the above manner. The effective beam width shown in FIG. 7 is calculated based on the profile calculated through the above steps.

As shown in FIG. 7, as the number of the malfunctioning transducers are increased (proportion of malfunctioning transducers is increased), both of the echo intensity and the effective beam width tend to be lowered, but the effective beam width begins to be lowered before the echo intensity begins to be lowered. In the example of FIG. 7, at the proportion of malfunctioning transducers of 25%, the effective beam width decreases by 6 dB or more although the echo intensity decreases only by approximately 2 dB.

As described above with reference to FIG. 1, if the effective beam width decreases excessively, the effective beam width of one unit of the selected transducers does not overlap the effective beam width of its adjacent unit of the selected transducers, so that a gap therebetween acts as an untested region where a flaw may be undetected. Since such decrease in the effective beam width occurs prior to the decrease in the echo intensity as described above, this cannot be sufficiently foreseen only by monitoring the decrease in the echo intensity. In order to appropriately diagnose abnormality of the array ultrasonic probe such as a malfunction of transducers included in every unit of the selected transducers, it is important to determine whether or not the effective beam width thereof is equal to a predetermined threshold value or less.

Based on the above described findings, the abnormality diagnosis method according to the present embodiment includes the following first to fourth steps.

(1) First Step:

selecting m (n>m≥1) transducers among n transducers, transmitting ultrasonic waves from the selected transducers toward the measurement target, and receiving echoes from the measurement target on these selected transducers.

(2) Second Step:

relatively scanning the measurement target by the selected transducers in the array direction of the transducers, and calculating the effective beam width of the selected transducers relative to the measurement target.

(3) Third Step:

repetitively executing the first step and the second step alternatively by changing over the multiple units of the selected transducers one by one.

(4) Fourth Step:

if any of the effective beam widths of the units of the selected transducers obtained in the third step is equal to a predetermined threshold value or less, determining that abnormality occurs on the unit of the selected transducers having this effective beam width equal to the predetermined threshold value or less.

If the array ultrasonic probe is installed in an inspection line for carrying out the ultrasonic testing on the plate material or the tubular material, the first and the second steps can be executed by employing any of the following procedures (a) to (c).

(a) Uninstalling the array ultrasonic probe from the inspection line for executing the ultrasonic testing and placing the array ultrasonic probe in a water tank equipped with a scanning mechanism; transmitting and receiving ultrasonic waves relative to the measurement target (steel ball with a diameter of ϕ 4 mm) in the water tank, so as to execute the first step; and allowing the array ultrasonic probe to scan in the array direction of the transducers using the scanning mechanism, so as to execute the second step.

(b) Placing the test material (such as a plate material) on which an artificial flaw is formed in the inspection line with the array ultrasonic probe installed in the inspection line for executing the ultrasonic testing; transmitting and receiving ultrasonic waves relative to an artificial flaw formed on the test material, so as to execute the first step; and relatively scanning the test material by the array ultrasonic probe in the array direction of the transducers, so as to execute the second step.

(c) Placing a tubular on which an artificial flaw is formed in the inspection line in such a manner that the axial direction of the tube is disposed substantially parallel to the array direction of the transducers and the array ultrasonic probe is installed in the inspection line for executing the ultrasonic testing, and then transmitting and receiving ultrasonic waves toward the artificial flaw on the tube, so as to execute the first step; and spirally conveying the tube in its axial direction or scanning the tube by the array ultrasonic probe in its axial direction with the tube rotated in its circumferential direction, so as to execute the second step.

It should be noted that the procedure (a) is not practical if the array ultrasonic probe is not readily uninstalled from the inspection line. In the procedures (b) and (c), the array ultrasonic probe is unnecessary to be uninstalled from the inspection line, but the array ultrasonic probe is necessary to relatively scan the test material in order to calculate the effective beam width, which complicates the procedure.

A method of relatively readily calculating the effective beam width may include such a method that prepares another array ultrasonic probe (alternative ultrasonic probe) as an alternative to the array ultrasonic probe for diagnosing abnormality (ultrasonic probe for diagnostic target) that is installed in the inspection line, calculates the effective beam width of this alternative ultrasonic probe out of the inspection line, and calculates (estimates) the effective beam width of the ultrasonic probe for diagnostic target based on this calculated value.

Specifically, abnormality of the ultrasonic probe for diagnostic target may be estimated by executing: a step of transmitting ultrasonic waves from the respective transducers included in the ultrasonic probe for diagnostic target and receiving echoes from the measurement target on these transducers; a step of preparing an alternative ultrasonic probe having the same configuration as that of the array ultrasonic probe for diagnostic target, transmitting ultrasonic waves from the respective transducers included in the alternative ultrasonic probe toward the measurement target, receiving the echo intensity from the measurement target on these transducers, and adjusting the flaw detection sensitivity and/or the transmission voltage of each transducer included in the alternative ultrasonic probe such that the echo intensity from the measurement target received on each transducer of the alternative ultrasonic probe is equal to the echo intensity received on each transducer included in the ultrasonic probe for diagnostic target; and also executing the first to the fourth steps on the alternative ultrasonic probe after adjusted.

An alternative ultrasonic probe having the same configuration denotes an ultrasonic probe including at least n transducers and having the substantially same center frequency and transducer width in the array direction as those of the ultrasonic probe for diagnostic target.

According to the aforementioned method, as described with reference to FIG. 5A, if the measurement target is the plate material P1, and the size (size in the array direction of the transducers included in the ultrasonic probe for diagnostic target) of the plate material P1 is equal to or more than the side (size in the array direction of the transducers) of the ultrasonic probe for diagnostic target, it is simply needed to transmit ultrasonic waves from the respective transducers included in the ultrasonic probe for diagnostic target toward the upper surface of the plate material P1, and to receive echoes from the bottom surface of the plate material P1 on these transducers. In other words, it is possible to relatively easily calculate (estimate) the effective beam width of the ultrasonic probe for diagnostic target in the state in which the ultrasonic probe for diagnostic target is installed in the inspection line and without requiring the ultrasonic probe for diagnostic target to scan relatively for the purpose of calculating the effective beam width.

A method of relatively easily calculating the effective beam width may include, a numerical calculation approach using software for analyzing propagation of an ultrasonic wave (software for solving a wave equation using the finite element method). Such software is available on the market, and software called as "ComWAVE"™ developed by ITO-CHU Techno-Solutions Corporation may be applicable to this calculation approach.

Specifically, it is possible to estimate abnormality of the array ultrasonic probe by executing: a step of transmitting ultrasonic waves from the respective transducers included in the array ultrasonic probe toward the measurement target, and receiving echoes from the measurement target on these transducers; and a step of calculating the echo intensity from the measurement target to be received on each transducer of the array ultrasonic probe when transmitting the ultrasonic waves from each transducer included in the array ultrasonic probe toward the measurement target, by means of software for analyzing propagation of the ultrasonic waves, and adjusting parameters corresponding to the flaw detection sensitivity and/or the transmission voltage for each transducer such that a calculated value and a measured value of the echo intensity received on each transducer are equal to each other through the software; as well as executing the numerical calculation corresponding to the first step to the fourth step using the software having the adjusted parameters.

Figure 8:
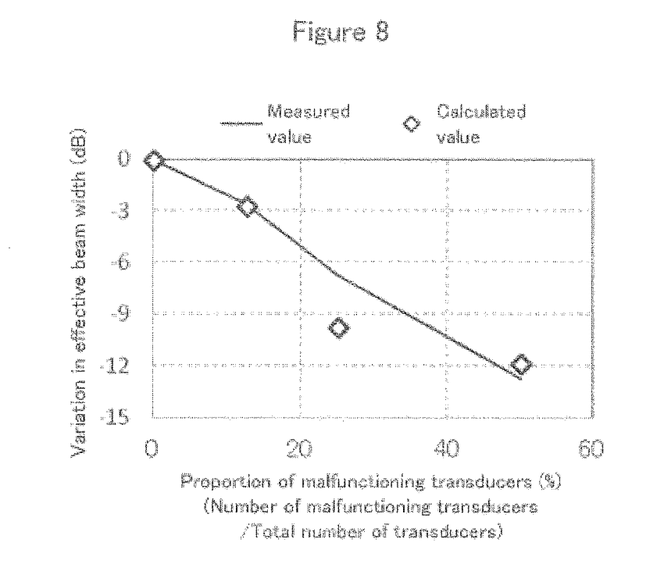
FIG. 8 is a graph of showing one example of the result from comparison between the measured values of the effective beam width of the selected transducers and the calculated values of the effective beam width of the selected transducers, which were obtained from a numerical calculation.

FIG. 8 is a graph of showing one example of the result from comparison between the measured, values of the effective beam width of the selected transducers and the calculated values of the effective beam width of the selected transducers, which were obtained from the above described numerical calculation.

The measured values of the effective beam width shown in FIG. 8 were measured in the same condition as that in the description with reference to FIG. 7. The calculated values of the effective beam width were obtained by executing the numerical calculation corresponding to the first step and the second step using the aforementioned software having the adjusted parameters.

As illustrated in FIG. 8, the measured values and the calculated values of the effective beam width are favorably correspondent to each other; and it should be appreciated that abnormality of the array ultrasonic probe can also be estimated through the numerical calculation.

REFERENCE SIGNS LIST

11 Transducer
100 Ultrasonic probe (array ultrasonic probe)
P1 Plate material
P2 Tubular material

The invention claimed is:

1. A method of adjusting flaw detection sensitivity on an ultrasonic probe including multiple transducers aligned linearly, the method comprising:
a step of disposing a plate material oppositely to the ultrasonic probe such that an upper surface of the plate material having the upper surface and a bottom surface that are approximately parallel to each other is disposed to be approximately parallel to an array direction of the multiple transducers, or disposing a tubular material having an inner surface and an outer surface oppositely to the ultrasonic probe such that an axial direction of the tubular material is disposed to be approximately parallel to the array direction of the multiple transducers;
a step of transmitting ultrasonic waves from each of the multiple transducers toward the upper surface of the plate material or the outer surface of the tubular material in a direction perpendicular to the upper surface or the outer surface, and receiving a bottom surface echo from the bottom surface of the plate material wherein the bottom surface does not have a flaw, or an inner surface echo from the inner surface of the tubular material wherein the inner surface does not have a flaw, on each of the multiple transducers; and
a step of adjusting flaw detection sensitivity of each of the multiple transducers wherein an intensity of the bottom surface echo or the inner surface echo received on each of the multiple transducers is adjusted so that the intensities for each of the multiple transducers are all substantially equal,
wherein the method is performed before an angle beam testing is performed using the ultrasonic probe.

2. A method of performing angle beam testing using an ultrasonic probe including multiple transducers aligned linearly, the method comprising:
a process of adjusting flaw detection sensitivity on the ultrasonic probe; and
a process of performing angle beam testing,
the process of adjusting flaw detection sensitivity on the ultrasonic probe comprising:
a step of disposing a plate material oppositely to the ultrasonic probe such that an upper surface of the plate material having the upper surface and a bottom surface that are approximately parallel to each other is disposed to be approximately parallel to an array direction of the multiple transducers, or disposing a tubular material having an inner surface and an outer surface oppositely to the ultrasonic probe such that an axial direction of the tubular material is disposed to be approximately parallel to the array direction of the multiple transducers;
a step of transmitting ultrasonic waves from each of the multiple transducers toward the upper surface of the plate material or the outer surface of the tubular material in a direction perpendicular to the upper surface or the outer surface, and receiving a bottom surface echo from the bottom surface of the plate material wherein the bottom surface does not have a flaw, or an inner surface echo from the inner surface of the tubular material wherein the inner surface does not have a flaw, on each of the multiple transducers; and
a step of adjusting flaw detection sensitivity of each of the multiple transducers wherein an intensity of the bottom surface echo or the inner surface echo received on each of the multiple transducers is adjusted so that the intensities for each of the multiple transducers are all substantially equal,
the process of performing angle beam testing comprising a step of performing an angle beam testing using the ultrasonic probe after adjusting flaw detection sensitivity of the multiple transducers.

* * * * *